United States Patent [19]

Kuwada et al.

[11] 4,049,812
[45] Sept. 20, 1977

[54] BENZODIAZEPINE CARBOXAMIDES AND PHARMACEUTICAL COMPOSITIONS WITH CENTRAL NERVOUS SYSTEM ACTIVITY

[75] Inventors: Yutaka Kuwada; Hideaki Natsugari; Kanji Meguro, all of Hyogo, Japan

[73] Assignee: Takeda Chemical Industries, Ltd., Osaka, Japan

[21] Appl. No.: 572,943

[22] Filed: Apr. 30, 1975

[30] Foreign Application Priority Data

May 7, 1974 Japan ................................. 49-51033

[51] Int. Cl.$^2$ ..................... A61K 31/44; C07D 223/16
[52] U.S. Cl. ................... 424/263; 260/295 A; 260/243.3; 424/248.54; 424/248.53
[58] Field of Search ................. 260/295 A; 424/244, 424/263

[56] References Cited

U.S. PATENT DOCUMENTS

| 3,767,661 | 10/1973 | Hester, Jr. ............... | 260/295 T |
| 3,870,714 | 3/1975 | Gagneux et al. ........... | 260/247.5 EP |
| 3,905,956 | 9/1975 | Derieg et al. ............. | 260/295 T |
| 3,914,215 | 10/1975 | Tachikawa et al. ......... | 260/239.3 T |

Primary Examiner—Norman A. Drezin
Attorney, Agent, or Firm—Burgess, Ryan and Wayne

[57] ABSTRACT

There is disclosed a novel heterocyclic compound of the general formula:

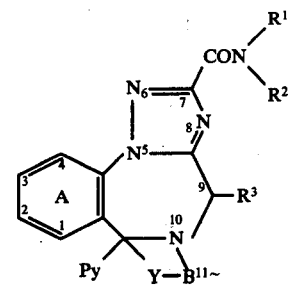

wherein each of $R^1$ and $R^2$ represents hydrogen atom, or an alkyl group which may be substituted by alkyl-substituted amino, hydroxy or alkoxy group, or $R^1$ and $R^2$ may form a heterocyclic ring together with the nitrogen atom adjacent thereto; $R^3$ represents hydrogen atom or a lower alkyl group; $P_y$ represents a pyridyl group; B represents a lower alkylene group which may have lower alkyl group as a substituent; Y represents oxygen atom, sulfur atom or —NH— group; and ring A is either unsubstituted or substituted by halogen atom, nitro, lower alkyl, lower alkoxy or polyhalo-lower alkyl group. This class of compounds is found to be useful as medicine in human and animal therapy, which act on the central nervous system, for example, muscle relaxants, anticonvulsants, sedatives, minor tranquilizers. There is also disclosed intermediates for the production of said compound.

21 Claims, No Drawings

BENZODIAZEPINE CARBOXAMIDES AND PHARMACEUTICAL COMPOSITIONS WITH CENTRAL NERVOUS SYSTEM ACTIVITY

This invention relates to heterocyclic compounds useful as medicines which are represented by the general formula (I):

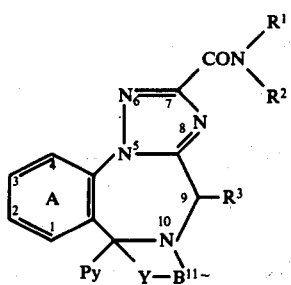

(I)

wherein each of $R^1$ and $R^2$ represents hydrogen atom, or an alkyl group which may be substituted by alkyl-substituted amino, hydroxy or alkoxy group, or $R^1$ and $R^2$ may form a heterocyclic ring together with the nitrogen atom adjacent thereto; $R^3$ represents hydrogen atom or a lower alkyl group; Py represents a pyridyl group; B represents a lower alkylene group which may have lower alkyl group as substituent; Y represents an oxygen or sulfur atom or an —NH— group; and the ring A is either unsubstituted or substituted by halogen atom, nitro, lower alkyl, lower alkoxy or polyhalo-lower alkyl group; and to processes for producing the same.

The present invention is further concerned with novel compounds having the following general formula (II) which are useful as intermediates for the production of the heterocyclic compounds of the general formula (I):

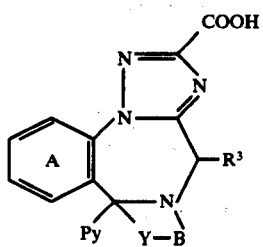

(II)

wherein $R^3$, Py, Y, B and the ring A are as defined above, and the carboxyl group may be in the form of a reactive derivative thereof.

The compounds (I) have pharmacological effects acting on the central nervous system such as muscle relaxant, anticonvulsant, sedative, antianxiety, tranquilizing and sleep inducing effects and are useful as medicines in human and animal therapy such as muscle relaxants, anticonvulsants, sedatives, antianxiety agents, minor tranquilizers and hypnotics.

In the aforesaid formulae, the alkyl groups represented by $R^1$ and $R^2$ are preferably lower alkyl groups having 1 to 6 carbon atoms, and the alkyl group may be straight, branched or cyclic. Examples of such alkyl groups include methyl, ethyl, propyl, isopropyl, butyl, isobutyl, sec-butyl, tert-butyl, pentyl, hexyl, cyclopropylmethyl, cyclopentyl and cyclohexyl groups. Among them, a lower alkyl group having 1 to 3 carbon atoms is preferred. When the alkyl groups represented by $R^1$ and $R^2$ are substituted by alkyl-substituted amino, hydroxy or alkoxy groups, any number, preferably 1 to 2, of these substituents may be at optional positions of the alkyl groups respresented by $R^1$ and/or $R^2$. The most preferable number of the substituents is one. The alkyl-substituted amino groups are exemplified by mono- or di-alkylamino groups whose alkyl moiety is lower alkyl groups having 1 to 4 carbon atoms (e.g. dimethylamino, diethylamino, dipropylamino, dibutylamino, methylamino, ethylamino, propylamino and butylamino). Among them, dialkylamino group is preferred. The alkoxy groups are exemplified by lower alkoxy groups having 1 to 4 carbon atoms (e.g. methoxy, ethoxy, propoxy and butoxy groups). When $R^1$ and $R^2$ form a heterocyclic ring together with the nitrogen atom adjacent thereto, the said heterocyclic ring is preferably a 5- to 6-membered ring, which may contain another 1 to 2 nitrogen and/or oxygen atoms as a hetero atom, and examples thereof are pyrrolidine, piperidine, piperazine, 4-substituted piperazines (e.g. 4-methylpiperazine, 4-(2-hydroxyethyl)-peperazine, etc.), morpholine, etc. As the substituents represented by each of $R^1$ and $R^2$, lower alkyl group having 1 to 3 carbon atoms and hydrogen atom are particularly preferred.

The lower alkyl group represented by $R^3$ is preferably one having 1 to 4 carbon atoms, and includes, for example, methyl, ethyl, propyl, isopropyl, butyl, isobutyl, sec-butyl and tert-butyl groups. As the substituent represented by $R^3$, hydrogen atom is most preferred.

When ring A is substituted by a halogen atom or nitro, lower alkyl, lower alkoxy or polyhalo-lower alkyl group, the number of said substituents is optional at any substitutable positions of ring A. The most preferable number of the substituents is one. The halogen atom which is the substituent of ring A includes fluorine, chlorine, bromine and iodine. The lower alkoxy group which is the substituent of the ring includes, for example, lower alkoxy groups having 1 to 4 carbon atoms such as methoxy, ethoxy, propoxy and butoxy groups. The lower alkyl group which is the substituent of the ring A includes, for example, the same lower alkyl groups having 1 to 4 carbon atoms as those represented by $R^3$. The polyhalo-lower alkyl group which is the substituent of the ring A includes, for example, trifluoromethyl and trichloromethyl groups.

Among the substituents of ring A, a halogen atom is preferable and as the position of the substituent, the 2-position of the formula (I) is preferable.

The pyridyl groups represented by Py is represented by the formula

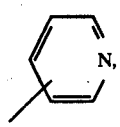

, and, among them, the 2-pyridyl group is preferred.

The lower alkylene group represented by B includes ethylene and trimethylene groups. When the said alkylene group has a lower alkyl group as substituent, the said alkyl group includes lower alkyl groups having 1 to 4 carbon atoms such as those represented by $R^3$.

As the group represented by Y, oxygen atom is preferred.

In the formulae described hereinafter, the ring A, $R^1$, $R^2$, $R^3$, Y, B and Py have the same meanings as defined above.

The compounds of the formula (I) can be produced by various processes, namely, 1. by a process which comprises [step (D)] reacting a compound represented by the general formula (III):

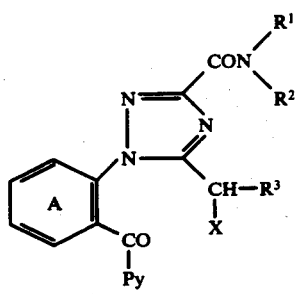

wherein X represents halogen atom or active ester residue of hydroxy group, with a compound represented by the general formula (VI):

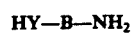

HY—B—NH$_2$   (VI)

2. by a process which comprises [step (B)] reacting a compound represented by the general formula (II):

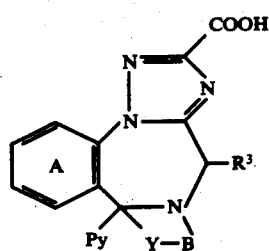

or its reactive derivative at the carboxyl group, with a compound represented by the general formula (V):

  (V)

3. by a process which comprises [step (C)] reacting a compound represented by the general formula (IV):

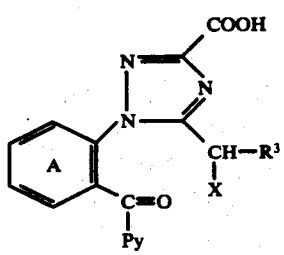  (IV)

wherein X is as defined above, or a reactive derivative at the carboxyl group thereof, with a compound represented by the general formula (V) to obtain a compound represented by the general formula (III):

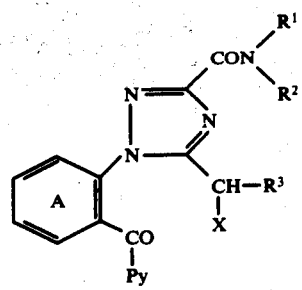  (III)

wherein Py, R$^1$ to R$^3$, X and the ring A are as defined above, and then [step (D)] reacting the thus obtained compound with a compound represented by the general formula (VI); and 4. by a process which compriese [step (A)] reacting a compound represented by the general formula (IV):

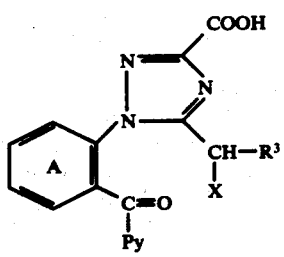  (IV)

wherein X and the ring A are as defined above, with a compound represented by the general formula (VI):

HY—B—NH$_2$   (VI)

to obtain a compound represented by the general formula (II):

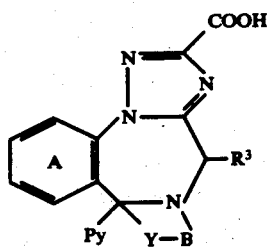  (II)

and then [step (B)] reacting the thus obtained compound, or a reactive derivative at the carboxyl group thereof, with a compound represented by the general formula (V):

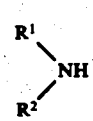  (V)

The reaction steps involved in the processes for producing the compounds (I) and (II) of the present invention are summarized in the following reaction scheme:

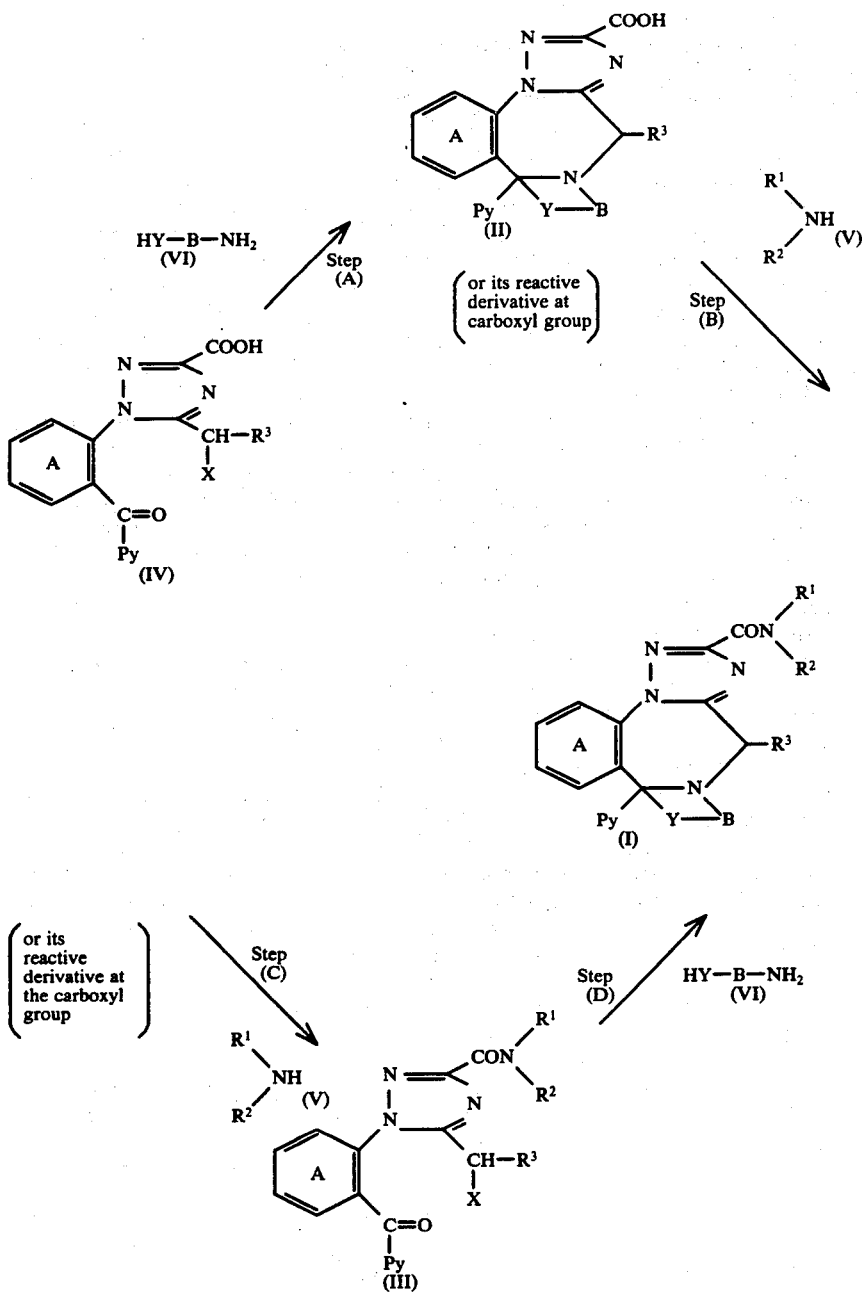

In the above formulae, the halogen atom represented by X includes fluorine, bromine, chlorine and iodine. The active ester residue of hydroxy group represented by X is exemplified by —O—mesyl, —O—tosyl group, etc. Among them, halogen atom is preferable as the group represented by X.

The steps (A) and (D) of the present invention are carried out by reacting compounds (IV) and (III), respectively, with a compound (VI). The amount of the compound (VI) to be used is ordinarily about 1 to 10 moles per mole of the compound (IV) or (III). The reaction between the compound (IV) or (III) and compound (VI) may proceed in the absence of a solvent, but proceeds more smoothly in the presence of a solvent. Examples of such solvent are alcohols (e.g. methanol, ethanol, propanol, butanol, etc.), aliphatic, aromatic or halogenated hydrocarbons (e.g. benzene, toluene, xylene, chloroform, dichloromethane, etc.), dialkylformamides (e.g. dimethyl- or diethyl-formamide, etc.), phenols, etc. The reaction temperature is suitably within the range of room temperature to about 200° C. When a solvent is used, the reaction temperature is usually around the boiling point of the solvent used.

When X of the compound (IV) or (III) is a halogen atom, a hydrogen halide corresponding to X is produced in the reaction of these steps. In order to accept the hydrogen halide, the compound (VI) may be used in excess, or alternatively there may be added to the reaction system a suitable basic substance (e.g. a tertiary amine such as triethylamine or pyridine, or an alkali metal carbonate or hydrogen carbonate such as sodium carbonate, potassium carbonate, sodium hydrogen carbonate or potassium hydrogen carbonate). When a compound (IV) or (III) wherein X is chlorine or bromine, is used as the starting material, the reaction may be more smoothly carried out in the presence of a catalytic or equimolar amount of potassium iodide or sodium iodide.

The steps (B) and (C) of the present invention are carried out by reacting a compound (II) and (IV), or reactive derivatives at the carboxyl group thereof respectively, with a compound (V).

Examples of the reactive derivative at the carboxyl group of the compound (II) or (IV) are lower alkyl esters whose alkyl moiety is lower alkyl having 1 to 4 carbon atoms (e.g. methyl ester, ethyl ester, propyl ester and butyl ester), active esters (e.g. 2,4-dinitrophenyl ester, pentachlorophenyl ester, N-hydroxysuccinimide ester, etc.), acid halides (e.g. acid chloride, acid bromide, etc.), and mixed acid anhydrides (e.g. mixed acid anhydrides with monomethyl carbonate or monoethyl carbonate). The above-mentioned alkyl esters can be produced by heating the compound (II) or (IV) with an alcohol (a lower alkanol having 1 to 4 carbon atoms) corresponding to the alkyl moiety of the ester in the presence of an acid catalyst (e.g. hydrochloric, sulfuric or p-toluenesulfonic acid) to the boiling point of the alcohol used. The said active esters can be easily produced by condensing the compound (II) or (IV) with a phenol corresponding to the ester moiety (e.g. 2,4-dinitrophenol or pentachlorophenol) or an N-hydroxysuccinimide by use of DCC (dicyclohexylcarbodiimide). The said acid halides can be easily produced by reacting the compound (II) or (IV) with phosphorus halogenides or phosphorus oxyhalogenides (e.g. phosphorus trichloride, phosphorus tribromide, phosphorus pentachloride or phosphorus oxychloride), or with thionyl chloride. The reaction is conducted in a suitable solvent (e.g. benzene, toluene, xylene, chloroform, dichloromethane or tetrahydrofuran) under ice-cooling or heating to about the boiling point of the solvent used. Further, the said mixed acid anhydrides can be easily produced in the conventional manner, for example, by reacting the compound (II) or (IV) with about 1 to 2 mole equivalent of a chlorocarbonic acid ester (e.g. an alkyl ester of chlorocarbonic acid) in a solvent (e.g. tetrahydrofuran, chloroform, dichloromethane, dioxane or dimethylformamide) in the presence of 1 to 2 mole equivalent of a basic substance (e.g. tertiary amine such as triethylamine) and under ice-cooling.

The thus prepared reactive derivative at the carboxyl group of the compound (II) or (IV) may be once ilolated and purified, if necessary. Alternatively, however, the reaction mixture itself containing the reactive derivative or the residue obtained by merely removing the solvent from the reaction mixture by distillation, may be used in the reaction of the step (B) or the step (C).

The reaction of the compound (II) or (IV), or a reactive derivative at the carboxyl group thereof, with the compound (V) may proceed even in the absence of a solvent since the starting compound (V) acts also as a solvent, but the reaction proceeds more smoothly by use of a solvent. Further, this reaction does not necessarily require the use of a condensing agent. However, when a free carboxylic acid of the general formula (II) or (IV) is used as one of the reactants, the reaction is preferably carried out in the presence of a condensing agent. As the solvent to be used in this reaction there may be used any solvent which is used for the production of the reactive derivatives at the carboxyl groups of the compound (II) or (IV), so far as it does not interfere with the reaction. Other solvents such as ethyl acetate may also be used. Furthermore, the condensing agent to be used in this reaction includes, for example, DCC, carbonyldiimidazole, etc. The amount of the starting compound (V) is usually about 1 to 10 moles per mole of the compound (II) or (IV) or its reactive derivative at the carboxyl group. When the condensing agent is used, the amount thereof may be about 1 to 1.5 moles per mole of the compound (II) or (IV). If the compound (V) is ammonia, it may be used in a suitable form such as liquid ammonia, aqueous ammonia or alcoholic ammonia (e.g. methanolic, ethanolic and propanolic ammonia). In this reaction, there are some cases where a basic substance (e.g. a tertiary organic amine such as triethylamine or N-methylpiperidine) may additionally be allowed to coexist for the acceleration of the reaction. In this case, the amount of the basic substance to be used is usually about 1 to 3 moles per mole of the compound (II) or (IV) or its reactive derivative at the carboxyl group. This reaction is preferably carried out with ice-cooling or at a temperature up to room temperature. If necessary, however, the reaction may be conducted at a higher temperature or in a sealed vessel with heating. In this case, the heating temperature is in the range of about 40° to about 150° C.

If the compound (V) is identical with the compound (VI), the object compound (I) can be obtained directly, without isolation of intermediate, by reacting the compound (IV), or its reactive derivative at the carboxyl group, with the compound (V) or (VI).

The compounds (IV), or lower alkyl esters thereof, which are starting compounds to be used in the present invention, can be synthesized according to the procedure shown by the following reaction scheme:

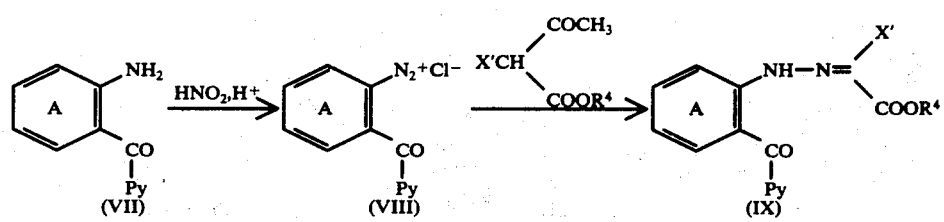

-continued

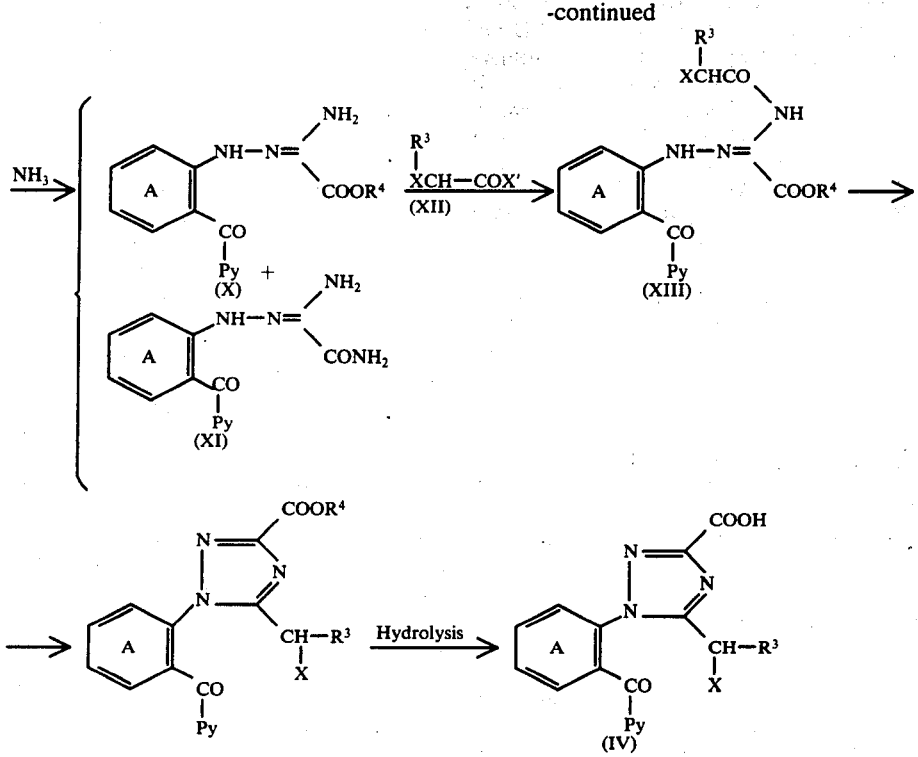

wherein R[4] represents a lower alkyl group (e.g. methyl, ethyl or propyl); X' represents a halogen atom (e.g. chlorine, bromine or iodine); and R[3], X, Py and the ring A are as defined above.

In the first place, a 2-aminobenzoylpyridine derivative (VII) is diazotized, and the resulting diazonium salt (VIII) is subjected to coupling with a 2-halogenoacetoacetic ester to produce a compound (IX). Subsequently, the compound (IX) is reacted with methanolic or ethanolic ammonia at −30° to 50° C., preferably 0° to 30° C., to obtain a compound (X). In this case, a compound (XI) may sometimes be produced as a by-product. Thereafter, the compound (X) is reacted with a compound (XII) in an inert solvent (e.g. benzene, toluene, tetrahydrofuran, chloroform or dichloromethane) at a temperature in the range from 0° to 100° C., preferably in the presence of an acid acceptor (e.g. sodium carbonate, potassium carbonate, sodium hydrogen carbonate or potassium hydrogen carbonate) to obtain a compound (XIII). This compound is then subjected to cyclization under dehydration to obtain a compound (IV'), a lower alkyl ester of the compound (IV), which is one of the starting compounds to be used in the present invention. The said cyclization under dehydration is carried out in a suitable solvent (e.g. methanol, ethanol, chloroform, dichloromethane, dioxane, tetrahydrofuran, benzene, toluene or xylene) at a temperature in the range from room temperature to the boiling point of the solvent used, preferably in the presence of an acid catalyst (e.g. acetic acid, propionic acid, hydrochloric acid, hydrobromic acid, sulfuric acid, phosphoric acid, methanesulfonic acid, benzenesulfonic acid and p-toluenesulfonic acid), a basic catalyst (e.g. triethylamine, pyridine, sodium carbonate, potassium carbonate, sodium hydroxide or potassium hydroxide) or imidazoles (e.g. imidazole, 2-methylimidazole). When sodium hydroxide or potassium hydroxide is used as said catalyst, the starting compound (IV), which is hydrolyzed product of the compound (IV') is produced depending on the amount of the catalyst used. Accordingly, when the said alkali is used in more than an equimolar amount to the compound (XIII), the compound (IV) can directly be obtained. It is of course possible to isolate the compound (IV') first and then hydrolyze the compound with alkali to obtain the compound (IV).

Further, by the following reaction using the compound (XI), which is a by-product of the reaction of the compound (IX) with ammonia, compound (XIV) which is the compound (III) wherein both R[1] and R[2] are hydrogen atoms can also be produced.

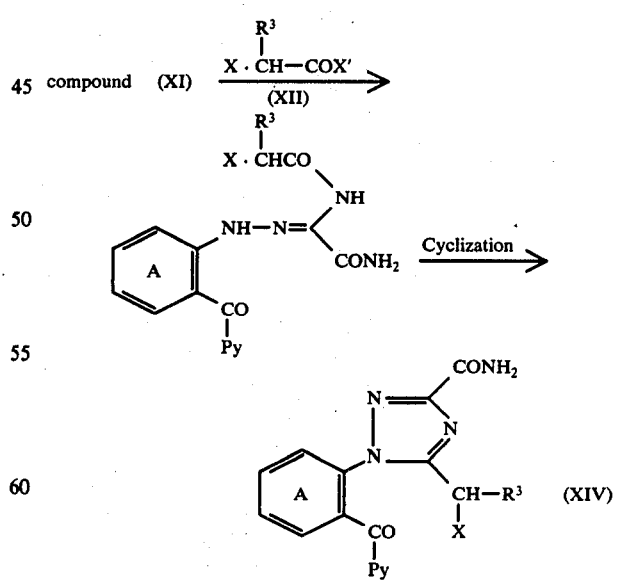

wherein R[3], X, X', Py and the ring A are as defined above.

When the object compounds (I) of the present invention are used as medicines in human and animal therapy such as muscle relaxants, anticonvulsants, sedatives, antianxiety agents, minor tranquilizers or hypnotics, they may be orally or parenterally administered as such or in a suitable form such as powders, granules, tablets, capsules, injections, etc. admixed with pharmaceutically acceptable carriers, excipients or diluents. The dose of the compound (I) to be administered varies with the kinds of diseases to be treated, the clinical conditions and the kind of the compound to be used, but usually falls within the range of from about 0.1 to 50 mg. for oral administration for an adult human per day.

Specific compounds as represented by the general formula (I) and (II), inclusive of those as shown in Examples which are set for illustrative but not limiting purpose, are as follows:

Compound (I)

1. 2-Bromo-11,12-dihydro-13a-(2-pyridyl)-9H, 13aH-oxazolo-[3,2-d]-s-triazolo[1,5-a][1,4]benzodiazepine-7-carboxamide
2. 2-Bromo-11,12-dihydro-11-methyl-13a-(2-pyridyl)-9H, 13aH-oxazolo[3,2-d]-s-triazolo[1,5-a][1,4]benzodiazepine-7-carboxamide
3. 2-Bromo-11,12-dihydro-12-methyl-13a-(2-pyridyl)-9H, 13aH-oxazolo[3,2-d]-s-triazolo[1,5-a][1,4]benzodiazepine-7-carboxamide
4. 2-Bromo-12,13-dihydro-14a-(2-pyridyl)- 9H, 11H, 14aH-[1,3]-oxazino[3,2-d]-s-triazolo[1,5-a][1,4]benzodiazepine-7-carboxamide
5. 2-Bromo-13a(2-pyridyl)-11,12,13,13a-tetrahydro-9H-imidazo-[1,2-d]-s-triazolo[1,5-a][1,4]benzodiazepine-7-(N-methyl)-carboxamide
6. 2-Bromo 11,12-dihydro-13a-(2-pyridyl)-9H,13aH-thiazolo-[3,2-d]-s-triazolo-[1,5-a][1,4]benzodiazepine-7-carboxamide
7. 2-Bromo-11,12-dihydro-13a-(4-pyridyl)-9H,13aH-oxazolo-[3,2-d]-s-triazolo[1,5-a][1,4]benzodiazepine-7-carboxamide
8. 2-Bromo-11,12-dihydro-9-methyl-13a-(2-pyridyl)-9H,13aH-oxazolo[3,2-d]-s-triazolo[1,5-a][1,4]benzodiazepine-7-carboxamide
9. 2-Bromo-11,12-dihydro-13a-(2-pyridyl)-9H,13aH-oxazolo[3,2-d]-s-triazolo[1,5-a][1,4]benzodiazepine-7-(N-methyl)-carboxamide
10. 2-Bromo-11,12-dihydro-11-methyl-13a-(2-pyridyl)-9H,13aH-oxazolo[3,2-d]-s-triazolo[1,5-a][1,4]benzodiazepine-7-(N-methyl)carboxamide
11. 2-Bromo-11,12-dihydro-12-methyl-13a-(2-pyridyl)-9H,13aH-oxazolo[3,2-d]-s-triazolo[1,5-a][1,4]benzodiazepine-7-(N-methyl)carboxamide
12. 2-Bromo-11,12-dihydro-13a-(2-pyridyl)-9H,13aH-oxazolo[3,2-d]-s-triazolo[1,5-a][1,4]benzodiazepine-7-(N-ethyl)carboxamide
13. 2-Bromo-11,12-dihydro-13a-(2-pyridyl)-9H,13aH-oxazolo-[3,2-d]-s-tria[1,5-a][1,4]benzodiazepine-7-(N-(2-hydroxyethyl)]carboxamide
14. 2-Bromo-11,12-dihydro-11-methyl-13a-(2-pyridyl)-9H,13aH-oxazolo[3,2-d]-s-triazolo[1,5-a][1,4]benzodiazepine-7-[N-(2-hydroxyisopropyl)]carboxamide
15. 2-Bromo-11,12-dihydro-12-methyl-13a-(2-pyridyl)-9H,13aH-oxazolo[3,2-d]-s-triazolo[1,5-a][1,4]benzodiazepine-7-[N-(2-hydroxypropyl)]carboxamide
16. 2-Bromo-11,12-dihydro-13a-(2-pyridyl)-9H,13aH-oxazolo-[3,2-d]-s-triazolo[1,5- ][1,4]benzodiazepine-7-(N,N-dimethyl)-carboxamide
17. 2bromo-11,12-dihydro-11-methyl-13a-(2-pyridyl)-9H,13aH-oxazolo[3,2-d]-s-triazolo[1,5-a][1,4]benzodiazepine-7-(N,N-dimethyl)carboxamide
18. 2-Bromo-11,12-dihydro-12-methyl-13a-(2-pyridyl)-9H,13aH-oxazolo[3,2-d]-s-triazolo[1,5-a][1,4]benzodiazepine-7-(N,N-dimethyl)carboxamide
19. 2-Bromo-11,12-dihydro-13a-(2-pyridyl)-9H,13aH-oxazolo-[3,2-d]-s-triazolo[1,5-a][1,4]benzodiazepine-7-(N,N-diethyl)carboxamide
20. 2-Bromo-11,12-dihydro-13a-(2-pyridyl)-9H,13aH-oxazolo-[3,2-d]-s-triazolo[1,5-a][1,4]benzodiazepine-7-[N-(2-dimethylaminoethyl)]carboxamide
21. 2-Bromo-11,12-dihydro-11-methyl-13a-(2-pyridyl)-9H,13aH-oxazolo[3,2-d]-s-triazolo[1,5-A][1,4]benzodiazepine-7-[N-(2-dimethylaminoethyl)]carboxamide
22. 2-Bromo-11,12-dihydro-12-methyl-13a-(2-pyridyl)-9H,13aH-oxazolo[3,2-d]-s-triazolo[1,5-a][1,4]benzodiazepine-7-[N-(2-dimethylaminoethyl)]carboxamide
23. 2-Bromo-11,12-dihydro-13a-(2-pyridyl)-9H,13aH-oxazolo-[3,2-d]-s-triazolo[1,5-a][1,4]benzodiazepine-7-[N-(2-methoxyethyl)]carboxamide
24. 2-Bromo-11,12-dihydro-13a-(2-pyridyl)-7-pyrrolidinocarbonyl-9H,13aH-oxazolo[3,2-d]-s-triazolo[1,5-a][1,4]benzodiazepine
25. 2-Bromo-11,12-dihydro-7-piperidinocarbonyl-13a-(2-pyridyl)-9H, 13aH-oxazolo[3,2-d]-s-triazolo[1,5-a][1,4]benzodiazepine
26. 2-Bromo-11,12-dihydro-7-morpholinocarbonyl-13a-(2-pyridyl)-9H,13aH-oxazolo[3,2-d]-s-triazolo[1,5-a][1,4]benzodiazepine
27. 2-Bromo-11,12-dihydro-11-methyl-7-morpholinocarbonyl-13a-(2-pyridyl)-9H,13aH-oxazolo[3,2-d]-s-triazolo[1,5-a][1,4]-benzodiazepine
28. 2-Bromo-11,12-dihydro-12-methyl-7-morpholinocarbonyl-13a-(2-pyridyl)-9H,13aH-oxazolo[3,2-d]-s-triazolo[1,5-a][1,4]-benzodiazepine
29. 2-Bromo-11,12-dihydro-7-(4-methyl)piperazinocarbonyl-13a-(2-pyridyl)-9H,13aH-oxazolo[3,2-d]-s-triazolo[1,5-a][1,4]-benzodiazepine
30. 2-Bromo-11,12-dihydro-11-methyl-7-(4-methyl)-piperazino-carbonyl-13a-(2-pyridyl)-9H,13aH-oxazolo[3,2-d]-s-triazolo-[1,5-a][1,4]benzodiazepine
31. 2-Bromo-11,12-dihydro-12-methyl-7-(4-methyl)-piperazino-carbonyl-13a-(2-pyridyl)-9H,13aH-oxazolo[3,2-d]-s-triazolo-[1,5-a][1,4]benzodiazepine
32. 2-Bromo-11,12-dihydro-7-(4-ethyl)piperazinocarbonyl-13a-(2-pyridyl)-9H,13aH-oxazolo[3,2-d]-s-triazolo[1,5-a][1,4]-benzodiazepine
33. 2-Bromo-11,12-dihydro-7-[4-(2-hydroxyethyl)-piperazinocarbonyl]-13a-(2-pyridyl)-9H,13aH-oxazolo[3,2-d]-s-triazolo-[1,5-a][1,4]benzodiazepine
34. 2-Chloro-11,12-dihydro-13a-(2-pyridyl)-9H,13aH-oxazolo-[3,2-d]-s-triazolo[1,5-a][1,4]benzodiazepine-7-carboxamide
35. 2-Chloro-11,12-dihydro-11-methyl-13a-(2pyridyl)-9H,13aH-oxazolo[3,2-d]-s-triazolo[1,5-a][1,4]benzodiazepine-7-carboxamide
36. 2-Chloro-11,12-dihydro-12-methyl-13a-(2-pyridyl)-9H,13aH-oxazolo[3,2-d]-s-triazolo[1,5-a][1,4]benzodiazepine-7-carboxamide
37. 2-Chloro-11,12-dihydro-13a-(2-pyridyl)-9H,13aH-oxazolo-[3,2-d]-s-triazolo[1,5-a][1,4]benzodiazepine-7-(N-methyl)-carboxamide
38. 2 -Chloro-11,12-dihydro-11-methyl-13a-(2-pyridyl)-9H,13aH-oxazolo-[3,2-d]-s-triazolo[1,5-a][1,4]benzodiazepine-7-(N-methyl)carboxamide
39. 2-Chloro-11,12-dihydro-12-methyl-13a-(2-pyridyl)-9H,13aH-oxazolo-[3,2-d]-s-triazolo[1,5-a][1,4]benzodiazepine-7-(N-methyl)carboxamide 40. 2-Chloro-11,12-dihydro-13a-(2-pyridyl)-9H,13aH-oxazolo-[3,2-d]-s-triazolo[1,5-a][1,4]benzodiazepine-7-(N-ethyl)-carboxamide
41. 2-Chloro-11,12-dihydro-13a-(2-pyridyl)-9H,13aH-oxazolo-[3,2-d]-s-triazolo[1,5-a][1,4]benzodiazepine-7-[N-(2-hydroxyethyl)]carboxamide
42. 2-Chloro-11,12-dihydro-13a-(2-pyridyl)-9H,13aH-oxazolo-[3,2-d]-s-triazolo[1,5-a][1,4]benzodiazepine-7-(N,N-dimethyl)carboxamide
43. 2-Chloro-11,12-dihydro-11-methyl-13a-(2-pyridyl)-9H,13aH-oxazolo-[3,2-d]-s-triazolo[1,5-a][1,4]benzodiazepine-7-(N,N-dimethyl)carboxamide
44. 2-Chloro-11,12-dihydro-12-methyl-13a-(2-pyridyl)-9H,13aH-oxazolo-]3,2-d]-s-triazolo[1,5-a][1,4]benzodiazepine-7-(N,N-dimethyl)carboxamide
45. 2-Chloro-11,12-dihydro-13a-(2-pyridyl)-9H,13aH-oxazolo-[3,2-d]-s-triazolo[1,5-a][1,4]benzodiazepine-7-[N-(2-dimethylaminoethyl)]carboxamide
46. 2-Chloro-11,12-dihydro-7-morpholinocarbonyl-13a-(2-pyridyl)-9H,13aH-oxazolo-[3,2-d]-s-triazolo[1,5-a][1,4]benzodiazepine
47. 2-Chloro-11,12-dihydro-7-(4-methyl)piperazinocarbonyl-13a-(2-pyridyl)-9H,13aH-oxazolo[3,2-d]-s-triazolo[1,5-a]-[1,4]benzodiazepine
48. 2-Chloro-11,12-dihydro-7-piperidinocarbonyl-13a-(2-pyridyl)-9H,13aH-oxazolo-[3,2-d]-s-triazolo[1,5-a][1,4]benzodiazepine
49. 11,12-Dihydro-13a-(2-pyridyl)-9H,13aH-oxazolo[3,2-d]-s-triazolo[1,5-a][1,4]benzodiazepine-7-carboxamide
50. 11,12-Dihydro-11-methyl-13a-(2-pyridyl-9H,13aH-oxazolo-[3,2-d]-s-triazolo[1,5-a][1,4]benzodiazepine-7-carboxamide
51. 11,12-Dihydro-12-methyl-13a-(2-pyridyl)-9H,13aH-oxazolo-[3,2-d]-s-triazolo[1,5a][1,4]benzodiazepine-7-carboxamide
52. 11,12-Dihydro-14a-(2-pyridyl)-9H,13H,14aH-s-triazolo[1,5-a]-[1,3]oxazino[3,2-d][1,4]benzodiazepine-7-carboxamide
53. 11,12-Dihydro-7-morpholinocarbonyl-13a-(2-pyridyl)-9H,13aH-oxazolo-[3,2-d]-s-triazolo[1,5-a][1,4]benzodiazepine
54. 2,4-Dibromo-11,12-dihydro-13a-(2pyridyl)-9H,13aH-oxazolo-[3,2-d]-s-triazolo[1,5-a][1,4]benzodiazepine-7-carboxamide
55. 11,12-Dihydro-2-nitro-13a-(2-pyridyl)-9H,13aH-oxazolo-[3,2-d]-s-triazolo[1,5-a][1,4]benzodiazepine-7-carboxamide
56. 11,12-Dihydro-2-methyl-13a-(2-pyridyl)-9H,13aH-oxazolo-[3,2-d]-s-triazolo[1,5-a][1,4]benzodiazepine-7-carboxamide
57. 11,12-Dihydro-13a-(2-pyridyl)-2-trifluoromethyl-9H,13aH-oxazolo[3,2-d]-s-triazolo[1,5-a][1,4]benzodiazepine-7-carboxamide
58. 11,12-Dihydro-2-methoxy-13a-(2-pyridyl)-9H,13aH-oxazolo-[3,2-d]-s-triazolo[1,5-a][1,4]benzodiazepine-7-carboxamide Compound (II)

1. 2-Bromo-11,12-dihydro-13a-(2-pyridyl)-9H,13aH-oxazolo-[3,2-d]-s-triazolo[1,5-a][1,4]benzodiazepine-7-carboxylic acid
2. 2-Bromo-11,12-dihydro-11-methyl-13a-(2-pyridyl)-9H,13aH-oxazolo[3,2-d]-s-triazolo[1,5-a][1,4]benzodiazepine-7-carboxylic acid
3. 2-Bromo-11,12-dihydro-12-methyl-13a-(2-pyridyl)-9H,13aH-oxazolo[3,2-d]-s-triazolo[1,5-a][1,4]benzodiazepine-7-carboxylic acid
4. 2-Bromo-11,12-dihydro-14a-(2-pyridyl)-9H,13H,14aH-s-triazolo[1,5-a][1,3]oxazino[3,2-d][1,4]benzodiazepine-7-carboxylic acid
5. 2-Bromo-13a-(2-pyridyl)-11,12,13,13a-tetrahydro-9H-imidazo-[1,2-d]-s-triazolo[1,5-a][1,4]benzodiazepine-7-carboxylic acid
6. 2-Bromo-11,12-dihydro-13a-(2-pyridyl)-9H,13aH-thiazolo-[3,2-d]-s-triazolo[1,5-a][1,4]benzodiazepine-7-carboxylic acid
7. 2-Bromo-11,12-dihydro-13a-(4-pyridyl)-9H,13aH-oxazolo-[3,2-d]-s-triazolo[1,5-a][1,4]benzodiazepine-7-carboxylic acid
8. 2-Bromo-11,12-dihydro-9-methyl-13a-(2-pyridyl)-9H,13aH-oxazolo[3,2-d]-s-triazolo[1,5-a][1,4]benzodiazepine-7- carboxylic acid
9. 2-Chloro-11,12-dihydro-13a-(2-pyridyl)-9H,13aH-oxazolo-[3,2-d]-s-triazolo[1,5-a][1,4]benzodiazepine-7-carboxylic acid
10. 2-Chloro-11,12-dihydro-11-methyl-13a-(2-pyridyl)-9H,13aH-oxazolo[3,2-d]-s-triazolo[1,5-a][1,4]benzodiazepine-7-carboxylic acid
11. 2-Chloro-11,12-dihydro-12-methyl-13a-(2-pyridyl)-9H,13aH-oxazolo[3,2-d]-s-triazolo[1,5-a][1,4]benzodiazepine-7-carboxylic acid
12. 11,12-Dihydro-13a-(2-pyridyl)-9H,13aH-oxazolo[3,2-d]-s-triazolo[1,5-a][1,4]benzodiazepine-7-carboxylic acid
13. 2,4-Dibromo-11,12-dihydro-13a-(2-pyridyl)-9H,13aH-oxazolo-[3,2-d]-s-triazolo[1,5-a][1,4]benzodiazepine-7-carboxylic acid
14. 11,12-Dihydro-2-nitro-13a-(2-pyridyl)-9H,13aH-oxazolo[3,2-d]-s-triazolo[1,5-a][1,4]benzodiazepine-7-carboxylic acid
15. 11,12-Dihydro-2-methyl-13a-(2-pyridyl)-9H,13aH-oxazolo-[3,2-d]-s-triazolo[1,5-a][1,4]benzodiazepine-7-carboxylic acid
16. 11,12-Dihydro-13a-(2-pyridyl)-2-trifluoromethyl-9H,13aH-oxazolo[3,2-d]-s-triazolo[1,5-a][1,4]benzodiazepine-7-carboxylic acid
17. 11,12-Dihydro-2-methoxy-13a-(2-pyridyl)-9H,13aH-oxazolo-3,2-d]-s-triazolo[1,5-a][1,4]benzodiazepine-7-carboxylic acid The present invention is illustrated in more detail below with reference to preparative Examples and Examples, but the invention is not limited to the Examples.

Preparative Example I 12.0 Grams of 2-(2-aminobenzoyl)pyridine is added to a mixture of 120 ml. of acetic acid and 16 ml. of concentrated hydrochloric acid. To the resulting mixture is then added a solution of 4.60 g. of sodium nitrite in 60 ml. of water with stirring under ice-cooling (0° to 7° C.), followed by stirring for 15 minutes to give a diazonium salt solution.

Separately, a solution of 9.0 g. of sodium acetate (CH₃COONa.3H₂O) in 100 ml. of water is added to a solution of 11.0 g. of ethyl 2-chloroacetoacetate in 220 ml. of ethanol. To the resulting mixture is then added dropwise the aforesaid diazonium salt solution with stirring under ice-cooling. Then the whole mixture is stirred for 3 hours at room temperature. The reaction mixture is diluted with 500 ml. of water, and then extracted with benzene. The benzene layer is washed successively with water, aqueous sodium hydrogen carbonate solution and water, and dried over sodium sulfate. Thereafter, the solvent is removed by distillation to give ethyl [2-(2-pyridinecarbonyl)phenyl]azo-chloroacetate as crystals. Recrystallization from ether gives yellow needles, melting at 123° to 125° C.

Elemental analysis for $C_{16}H_{14}ClN_3O_3$:
Calculated: C 57.92, H 4.25, N 12.67 Found: C 58.08, H 4.17, N 12.63

Preparative Example 2

A mixture of 17.0 g. of ethyl [2-(2-pyridinecarbonyl)-phenyl]azo-chloroacetate in 180 ml. of dichloromethane and 200 ml. of 20% ethanolic ammonia is stirred at room temperature for 2 hours. The reaction mixture is diluted with water and then extracted with dichloromethane. The dichloromethane layer is washed with water, dried over sodium sulfate, and then the solvent is removed by distillation. The residue is subjected to a column chromatography using 150 g. of silica gel, and the fractions eluted with a mixture of n-hexane and acetone (3:2) are combined and concentrated to give [2-(2-pyridinecarbonyl)-phenyl]azo-aminoacetate as crystals. Recrystallization from ether-n-hexane gives orange needles, melting at 83° to 84° C.

Elemental analysis for $C_{16}H_{16}N_4O_3$:
Calculated: C 61.53, H 5.16, N 17.94 Found: C 61.72, H 5.15, N 17.92

After elution of the above-mentioned compound, the column is then eluted with a mixture of chloroform, methanol and ethyl acetate (85:10:5) to give [2-(2-pyridinecarbonyl)phenyl]azo-aminoacetamide as crystals. Recrystallization from chloroform gives orange needles, melting at 210° to 212° C.

Elemental analysis for $C_{14}H_{13}N_5O_2$:
Calculated: C 59.35, H 4.63, N 24.72 Found: C 59.41, H 4.34, N 24.56

Preparative Example 3

To a solution of 12.5 g. of ethyl [2-(2-pyridinecarbonyl)phenyl]azo-aminoacetate in 400 ml. of anhydrous benzene are added 11.4 g. of potassium carbonate and 8.0 ml. of chloroacetyl chloride. The resulting mixture is refluxed with stirring for 30 minutes, and then cooled. The resulting precipitate is collected by filtration, and partitioned between saturated aqueous sodium hydrogen carbonate solution and chloroform. The chloroform layer is separated, washed with water, dried over sodium sulfate, followed by evaporation of the solvent to give ethyl [2-(2-pyridinecarbonyl)phenyl]azo-(2-chloroacetamido)-acetate as crystals. Recrystallization from acetone-n-hexane gives yellow needles, melting at 160 to 162° C.

Elemental analysis for $C_{17}H_{17}ClN_4O_4$:
Calculated: C 55.60, H 4.41, N 14.41 Found: C 55.36, H 4.27, N 14.18

Preparative Example 4

A solution of 11.0 g. of ethyl [2-(2-pyridinecarbonyl)phenyl]azo-(2-chloroacetamido)acetate and 2.5 g. of 2-methylimidazole in 500 ml. of ethanol is refluxed for one hour, followed by evaporation of the solvent. The residue is made alkaline with saturated aqueous sodium hydrogen carbonate solution, and extracted with chloroform. The chloroform layer is washed with water and dried over sodium sulfate, followed by evaporation of the solvent to give ethyl 1-[2-(2-pyridinecarbonyl)-phenyl]-5-chloromethyl-1H-1,2,4-triazole-3-carboxylate as crystals. Recrystallization from acetone-n-hexane gives colorless prisms, melting at 129° to 130° C.

Elemental analysis for $C_{17}H_{15}ClN_4O_3$:
Calculated C 58.30, H 4.08, N 15.11 Found: C 58.51, H 3.97, N 14.85

Preparative Example 5

To a solution of 3.0 g. of ethyl 1-[2-(2-pyridinecarbonyl)phenyl]-5-chloromethyl-1H-1,2,4-triazole-3-carboxylate in 40 ml. of ethanol is added 9 ml. of 1N-sodium hydroxide solution with stirring at room temperature. After stirring for 20 minutes, the solvent is evaporated by distillation, and neutralized with 9 ml. of 1N-hydrochloric acid. The precipitated crystals are collected by filtration, washed successively with water, ethanol and ether and then dried to give 1-[2-(2-pyridinecarbonyl)phenyl]-5-chloromethyl-1H-1,2,4-triazole-3-carboxylic acid as crystals. Recrystallization from ethanol gives colorless prisms, melting at 204° to 206° C. (decomposition).

Elemental analysis for $C_{16}H_{11}ClN_4O_3$:
Calculated: C 56.07, H 3.24, N 16.35 Found: C 55.83, H 3.31, N 16.36

Preparative Example 6

To a solution of 0.85 g. of [2-(2-pyridinecarbonyl)phenyl]azo-aminoacetamide in 30 ml. of anhydrous benzene are added 0.42 g. of potassium carbonate and 1.0 ml. of chloroacetyl chloride. The mixture is refluxed with stirring for 45 minutes, and then cooled. The precipitated crystals are collected by filtration, and partitioned between saturated aqueous sodium hydrogen carbonate solution and chloroform. The chloroform layer is separated, washed with water, dried over sodium sulfate, and then the solvent is removed by distillation to give [2-(2-pyridinecarbonyl)phenyl]azo-(2-chloroacetamido)acetamide as crystals. Recrystallization from ethanol gives yellow needles, melting at 204° to 205° C. (decomposition).

Elemental anaylsis for $C_{16}H_{14}ClN_5O_4$:
Calculated: C 53.41, H 3.92, N 19.47 Found: C 53.15, H 3.79, N 19.50

Preparative Example 7

A solution of 0.3 g. of [2-(2-pyridinecarbonyl)-phenyl]azo-(2-chloroacetamido)acetamide and 0.82 g. of 2-methylimidazole in 12ml. of ethanol is refluxed for one hour and then cooled. The precipitated crystals are collected by filtration to give 1-[2-(2-pyridinecarbonyl)-phenyl]-5-chloromethyl-1H-1,2,4-triazole-3-carboxamide as crystals. Recrystallization from chloroform-ethanol gives colorless needles, melting at 228° to 229° C. (decomposition).

According to the same manner as in the above-mentioned Preparative Examples 1 to 7, such compounds as mentioned below can be produced.

Preparative Example 8

A. According to the same manner as in Preparative Example 1, 8.3 g. of 2-(2-amino-5-bromobenzoyl)pyridine is diazotized with nitrous acid and then subjected to coupling with 5.5g. of ethyl 2-chloroacetoacetate to give ethyl [4-bromo-2-(2-pyridinecarbonyl)phenyl]azo-chloroacetate as crystals. Recrystallization from ether gives yellow needles, melting at 155° to 156° C.

Elemental analysis for $C_{16}H_{13}BrClN_3O_2$:
Calculated: C 46.79, H 3.19, N 10.23 Found: C 47.05, H 3.11, N 10.24

B. According to the same manner as in Preparative Example 2, the thus prepared compound is reacted with ammonia to give ethyl [4-bromo-2-(2-pyridinecarbonyl)phenyl]azo-aminoacetate as crystals. Recrystallization from ether gives orange needles, melting at 156° to 157° C.

Elemental analysis for $C_{16}H_{15}BrN_4O_3$:

Calculated: C 49.12, H 3.86, N 14.32 Found: C 49.16, H 3.58, N 14.41

C. According to the same manner as in Preparative Example 3, the thus prepared compound is chloroacetylated to give ethyl [4-bromo-2-(2-pyridinecarbonyl)-phenyl]azo-(2-chloroacetamido)acetate as crystals. Recrystallization from acetone-n-hexane gives yellow needles, melting at 160° to 162° C.

Elemental analysis for $C_{18}H_{16}BrB1N_4O_4$:

Calculated: C 46.22, H 3.45, N 11.98 Found: C 46.06, H 3.24, N 12.09

D. According to the same manner as in Preparative Example 4, the thus obtained crystals are heated in the presence of 2-methylimidazole to give ethyl 1-[4-bromo-2-(2-pyridinecarbonyl)phenyl]-5-chloromethyl-1H-1,2,4-triazole-3-carboxylate as crystals. Recrystallization from ether gives colorless prisms, melting at 96° to 97° C.

Elemental analysis for $C_{18}H_{14}BrClN_4O_3$:

Calculated: C 48.07, H 3.14, N 12.46 Found: C 48.08, H 2.89, N 12.75

E. According to the same manner as in Preparative Example 5, ethyl 1-[4-bromo-2-(2-pyridinecarbonyl)-phenyl]-5-chloromethyl-1H-1,2,4-triazole-3-carboxylate is hydrolyzed with sodium hydroxide to give 1-[4-bromo-2-(2-pyridinecarbonyl)-phenyl]-5-chloromethyl-1H-1,2,4-triazole-3-carboxylic acid as crystals. Recrystallizations from ethanol gives colorless prisms, melting at 215° C to 217° C. (decomposition).

Elemental analysis for $C_{16}H_{10}BrClN_4O_3$:

Calculated: C 45.57, H 2.39, N 13.29 Found: C 45.74, H 2.33, N 13.22

Preparative Example 9

To a solution of 0.258 g. of 1-[2-(2-pyridinecarbonyl)-phenyl]-5-chloromethyl-1H-1,2,4-triazole-3-carboxylic acid in 7.5 ml. of chloroform are added 0.14 ml. of triethylamine and then 0.1 ml. of ethyl chlorocarbonate with ice-cooling. After stirring for 10 minutes, to the resulting mixture is added 0.5 ml. of concentrated aqueous ammonia, and the whole mixture is further stirred for 30 minutes. The precipitated crystals are collected by filtration, washed successively with water, ethanol and ether, and then dried to give 1-[2-(2-pyridinecarbonyl)phenyl]-5-chloromethyl-1H-1,2,4-triazole-3-carboxamide as crystals. The filtrate is extracted with chloroform and the chloroform layer is washed with water, dried over sodium sulfate, followed by evaporation of the solvent to give additional crystals identical with the abovementioned crystals. Recrystallization of the combined crystals from chloroform-ethanol gives colorless needles, melting at 228° to 229° C. (decomposition).

Elemental analysis for $C_{16}H_{12}ClN_5O_2$:

Calculated: C 56.23, H 3.54, N 20.49 Found: C 55.90, H 3.58, N 20.16

Preparative Example 10

To a solution of 0.516 g. of 1-[2-(2-pyridinecarbonyl)-phenyl]-5-chloromethyl-1H-1,2,4-triazole-3-carboxylic acid in 15 ml. of chloroform are added 0.28 ml. of triethylamine and then 0.2 ml. of ethyl chlorocarbonate with ice-cooling. After stirring for 10 minutes, to the resulting solution is added 0.20 ml. of morpholine and whole mixture is stirred for further 20 minutes. The reaction mixture is diluted with water and then extracted with chloroform. The chloroform layer is washed with water, dried over sodium sulfate, followed by evaporation of the solvent to give 5-chloromethyl-3-morpholinocarbonyl-1-[2-(2-pyridinecarbonyl)phenyl[-1H-1,2,4-triazole as crystals. Recrystallization from acetone-n-hexane gives colorless prisms, melting at 162° to 164° C.

Elemental analysis for $C_{20}H_{18}ClN_5O_3$:

Calculated: C 58.32, H 4.40, N 17.01 Found: C 58.33, H 4.41, N 16.66

Preparative Example 11

To a solution of 0.75 g. of 1-[4-bromo-2-(2-pyridinecarbonyl)phenyl]-5-chloromethyl-1H-1,2,4-triazole-3-carboxylic acid in 25 ml. of chloroform are added 0.35 ml. of triethylamine and then 0.24 ml. of ethyl chlorocarbonate under ice-cooling. After stirring for 10 minutes, to the resulting mixture is added 0.75 ml. of a 40% aqueous methylamine solution and the whole mixture is stirred for further 30 minutes. The reaction mixture is diluted with water and then extracted with chloroform. The chloroform layer is washed with water, dried over sodium sulfate, followed by evaporation of the solvent to give 1-[4-bromo-2-(2-pyridinecarbonyl)phenyl]-5-chloromethyl-1H-1,2,4-triazole-3-(N-methyl)carboxamide as crystals. Recrystallization from acetone gives colorless prisms, melting at 208° to 209° C. (decomposition).

Elemental analysis for $C_{17}H_{12}BrClN_5O_2$:

Calculated: C 47.08, H 2.79, N 16.15

Found: C 47.21, H 2.93, N 15.99

The same reaction as above is repeated, except that the 40% aqueous methylamine solution is replaced by concentrated aqueous ammonia, to give 1-[4-bromo-2-(2-pyridinecarbonyl(phenyl)-5-chloromethyl-1H-1,2,4-triazole-3-carboxamide. Recrystallization from ethanol gives colorless prisms, melting at 192° to 194° C. (decomposition).

Elemental analysis for $C_{16}H_{11}BrClN_5O_2$:

Calculated: C 45.68, H 2.64, N 16.65 Found: C 45.78, H 2.43, N 16.42

Preparative Example 12

The reaction in Preparative Example 11 is repeated, except that the aqueous methylamine solution is replaced by about 1.5 equivalents of piperdine, to give 1-[4-bromo-2-(2-pyridinecarbonyl)phenyl]-5-chloromethyl-3-piperidinocarbonyl-1-H-1,2,4-triazole from 1-[4-bromo-2-(2-pyridinecarbonyl)phenyl]-5-chloromethyl-1H-1,2,4-triazole-3-carboxylic acid as crystals. Recrystallization from acetone-n-hexane gives colorless prisms, melting at 213° to 215° C. (decomposition).

Elemental analysis for $C_{21}H_{19}BrClN_5O_2$:

Calculated: C 51.60, H 3.92, N 14.33

Found: C 51.71, H 3.60, N 14.34

Example 1

A solution of 0.23 g. of 5-chloromethyl-1[2-(2-pyridinecarbonyl)phenyl]-1H-1,2,4-triazole-3-carboxamide and 0.12 ml. of 2-aminoethanol in a mixed solvent of 10 ml. of ethanol and 2 ml. of chloroform is refluxed for 16 hours, and then the solvent is removed by distillation. The residue is diluted with water and the mixture is then extracted with chloroform. The chloroform layer is washed with water, dried over sodium sulfate, followed by evaporation of the solvent to give 11,12-dihydro-13a-(2-pyridyl)-9H,13a H-oxazolo[3,2-d]-s-triazolo[1,5-a][1,4]benzodiazepine-7-carboxamide as crystals. Recrystallization from acetone gives colorless prisms, melting at 211° to 212° C.

Elemental analysis for $C_{18}H_{16}N_6O_2$:
Calculated: C 62.06, H 4.63, N 24.13 Found: C 61.83, H 4.59, N 23.83

Example 2

A solution of 0.25 g. of 1-[4-bromo-2-(2-pyridinecarbonyl)phenyl]-5-chloromethyl-1H-1,2,4-triazole-3-carboxamide and 0.12 ml. of 2-aminopropanol in 10 ml. of ethanol is refluxed for 17 hours, and then the solvent is removed by distillation. The residue is diluted with water and the mixture is then extracted with chloroform. The chloroform layer is washed with water, dried over sodium sulfate, followed by evaporation of the solvent to give 2-bromo-11,12-dihydro-12-methyl-13a-(2-pyridyl)-9H,13aH-oxazole[3,2-d]-s-triazolo[1,5-a][1,4]benzodiazepine-7-carboxamide as crystals. Recrystallization from acetone gives colorless prisms, melting at 252° to 254° C. (decomposition).

Elemental analysis for $C_{19}H_{17}BrN_6O_2$:
Calculated: C 51.71, H 3.88, N 19.05 Found: C 51.99, H 4.09, N 18.80

In a similar manner to those described in any of Examples 1 and 2, such compounds as mentioned below can be produced from corresponding 1-(2-pyridinecarbonylphenyl)-5-halomethyl-1H-1,2,4-triazole derivatives.

Example 3

The procedure of Example 1 is repeated, except that the 2-aminoethanol is replaced by 2-aminopropanol, to give 11,12-dihydro-12-methyl-13a-(2-pyridyl)-9H,13aH-oxazolo-[3,2-d]-s-triazolo[1,5-a][1,4]benzodiazepine-7-carboxamide as crystals. Recrystallization from ethanol gives colorless needles, melting at 241° to 243° C. (decomposition).

Elemental analysis for $C_{19}H_{18}N_6O_2$:
Calculated: C 62.97, H 5.01, N 23.19 Found: C 62.75, H 4.97, N 23.32

Example 4

The procedure of Example 1 is repeated, except that the 2-aminoethanol is replaced by 3-aminopropanol, to give 12,13-dihydro-14a-(2-pyridyl)-9H,11H,14aH-[1,3]oxazino[3,2-d]-s-triazolo[1,5-a][1,4]benzodiazepine-7-carboxamide as crystals. Recrystallization from acetone gives colorless prisms, melting at 215° to 216° C.

Elemental analysis for $C_{19}H_{18}N_6O_2$:
Calculated: C 62.97, H 5.01, N 23.19 Found: C 62.99, H 5.13, N 22.96

Example 5

According to the method of Example 1, 5-chloromethyl-3-morpholinocarbonyl-1-[2-(2-pyridinocarbonyl)phenyl]-1H-1,2,4-triazole is reacted with 2-aminoethanol to give 11,12-dihydro-7-morpholinocarbonyl-13a-(2-pyridyl)-9H,13aH-oxazolo-[3,2-d]-s-triazolo[1,5-a][1,4]benzodiazepine as crystals. Recrystallization from acetone gives colorless prisms, melting at 212° to 213° C.

Elemental analysis for $C_{22}H_{22}N_6O_3$:
Calculated: C 63.14, H 5.30, N 20.09 Found: C 63.46, H 5.39, N 20.14

Example 6

The procedure of Example 2 is repeated, except that the 2-aminopropanol is replaced by 2-aminoethanol, to give 2-bromo-11,12-dihydro-13a-(2-pyridyl)-9H,13aH-oxazolo[3,2-d]-s-triazolo[1,5-a][1,4]benzodiazepine-7-carboxamide as crystals. Recrystallization from acetone gives colorless needles, melting at 237° to 238° C.

Elemental analysis for $C_{18}H_{15}BrN_6O_2$:
Calculated: C 50.60, H 3.54, N 19.67 Found: C 50.28, H 3.24, N 19.67

Example 7

According to the method of Example 1, 1-[4-bromo-2-(2-pyridinecarbonyl)phenyl]-5-chloromethyl-1H-1,2,4-triazole-3-(N-methyl)carboxamide is reacted with 2-aminoethanol to give 2-bromo-11,12-dihydro-13a-(2-pyridyl)-9H,13aH-oxazolo[3,2-d]-s-triazolo[1,5-d][1,4]benzodiazepine-7-(N-methyl)carboxamide as crystals. Recrystallization from acetone gives colorless prims melting at 224° to 225° C.

Elemental analysis for $C_{19}H_{17}BrN_6O_2$:
Calculated: C 51.71, H 3.88, N 19.05 Found: C 51.74, H 3.78, N 18.96

Example 8

The procedure of Example 7 is repeated, except that the 2-aminoethanol is replaced by ethylenediamine, to give 2-bromo-13a-(2-pyridyl)-11,12,13,13a-tetrahydro-9H-imidazo[1,2-d]-s-triazolo[1,5-a][1,4]benzodiazepine-7-(N-methyl) carboxamide as crystals, melting at 250° to 251° C.

Elemental analysis for $C_{19}H_{18}BrN_7O$:
Calculated: C 51.82, H 4.12, N 22.27 Found: C 51.73, H 4.17, N 22.10

Example 9

A solution of 0.3 g. of ethyl 1-[4-bromo-2-(2-pyridinecarbonyl)phenyl]-5-chloromethyl-1H-1,2,4-triazole-3-carboxylate and 0.15 ml. of 2-aminoethanol in 10 ml. of ethanol is refluxed for 24 hours, and then the solvent is removed by distillation. The residue is diluted with water and the mixture is extracted with chloroform. The chloroform layer is treated in the same manner as in the foregoing Examples to give 2-bromo-11,12-dihydro-13a-(2-pyridyl)-9H,13aH-oxazolo[3,2-d]-s-triazolo[1,5-a][1,4]benzodiazepine-7-[N-(2-hydroxyethyl)]carboxamide as crystals, melting at 177° to 179° C.

Elemental analysis for $C_{20}H_{19}BrN_6O_3$:
Calculated: C 50.96, H 4.06, N 17.83 Found: C 50.99, H 3.98, N 17.79

Example 10

A solution of 0.25 g. of 1-[4-bromo-2-(2-pyridinecarbonyl)phenyl]-5-chloromethyl-1H-1,2,4-triazole-3-carboxylic acid and 0.1 ml. of 2-aminoethanol in 15 ml. of ethanol and 5 ml. of chloroform is refluxed for 24 hours, and the reaction mixture is concentrated under reduced pressure. The resulting precipitated crystals are collected by filtration to give a ¼ hydrate of an ethanolamine salt of 2-bromo-11,12-dihydro-13a-(2-pyridyl)-9H,13aH-oxazolo[3,2-d]-s-triazolo[1,5-a][1,4]bwnzodiazepine-7-carboxylic acid. Recrystallization from methanol-ethanol (1:1) gives colorless prisms, melting at 216° to 218° C. (decomposition).

Elemental analysis for $C_{18}H_{14}BrN_5O_3NH_2CH_2CH_2OH.1/2H_2O$:
Calculated: C 48.20, H 4.45, N 16.87 Found: C 48.36, H 4.28, N 16.90

Example 11

0.1 Gram of 2-bromo-11,12-dihydro-13a-(2-pyridyl)-9H,13aH-oxazolo[3,2-d]-s-triazolo[1,5-a][1,4]benzodiazepine-7-carboxylic acid ethanolamine salt (½ hydrate) is partitioned between 20 ml. of chloroform and 1 ml. of 1N-hydrochloric acid. Thereafter, the chloroform layer is separated, washed with water and dried over sodium sulfate, and then the solvent is removed by distillation, whereby free carboxylic acid is obtained as an oily substance, which is then dissolved in 4ml. of chloroform. To the resulting solution are added 0.05 ml. of triethylamine and then 0.04 ml. of ethyl chlorocarbonate under ice-cooling and stirring. The whole mixture is stirred for 10 minutes, and to the resultant is added 0.5 ml. of a 40% aqueous methylamine solution, followed by stirring for further 30 minutes. Then, the reaction mixture is diluted with water and then extracted with chloroform. The chloroform layer is washed with water, dried over sodium sulfate, followed by evaporation of the solvent to give 2-bromo-11,12-dihydro-13a-(2-pyridyl)-9H,13aH-oxazolo[3,2-d]-s-triazolo[1,5-a][1,4]-benzodiazepine-7-(N-methyl)carboxamide as crystals. Recrystallization from acetone gives colorless prisms, melting at 224° to 225° C. The thus obtained product is identical with that obtained in Example 7 in respect with melting point and IR and NMR Spectrum thereof.

Example 12

An example of practical recipe in which a compound of this invention is utilized as transquilizer is as follows:

Tablet

| | | | |
|---|---|---|---|
| | 2-bromo-11,12-dihydro-12-methyl-13a-(2-pyridyl)-9H,13aH-oxazolo[3,2-d]-s-triazolo[1,5-a][1,4]-benzodiazepine-7-carboxamide | 1 | mg |
| (2) | lactose | 73 | mg |
| (3) | corn starch | 40 | mg |
| (4) | hydroxypropyl cellulose | 5.5 | mg |
| (5) | magnesium stearate | 0.5 | mg |
| | | 120.0 | mg per tablet |

(1), (2), 9/10 quantity of (3), and (4) are thoroughly mixed and the mixture is granulated by wet granulation method. Remaining quantity of (3), and (5) are added to the granules and compressed into tablets. Thus prepared tablets may further be coated with suitable coating materials, e.g. sugar.

What we claim is:
1. A compound of the formula (I):

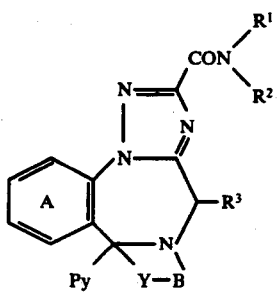

wherein each $R^1$ and $R^2$ represents a hydrogen atom, or an alkyl group having form 1 to 6 carbon atoms, said alkyl group being unsubstituted or substituted by a $C_{1-4}$ alkylamino, hydroxy or $C_{1-4}$ alkoxy group, or $R^1$ and $R^2$ together with the nitrogen atom adjacent thereto forming piperidino or pyrrolidino; $R^3$ represents a hydrogen atom or a lower alkyl group having 1 to 4 carbon atoms; Py represents a pyriduyl group; B represents an ethylene group or ethylene which is substituted by lower alkyl having 1 to 4 carbon atoms; Y represents an oxygen atom; and the ring A is either unsubstituted or substituted by a halogen atom, nitro, lower alkyl having 1 to 4 carbon atoms, lower alkoxy having 1 to 4 carbon atoms, trifluoromethy, or trichloromethyl group.

2. A compound as claimed in claim 1, wherein both $R^1$ and $R^2$ are hydrogen.

3. A compound as claimed in claim 1, wherein both $R^1$ and $R^2$ are alkyl groups each having 1 to 3 carbon atoms.

4. A compound as claimed in claim 1, wherein one of $R^1$ and $R^2$ is an alkyl group having 1 to 3 carbon atoms and the other is a hydrogen atom.

5. A compound as claimed in claim 2, wherein the ring A is substituted by a halogen atom.

6. A compound as claimed in claim 5, wherein the halogen atom is substituted in the 2-position of the ring A.

7. A compound as claimed in claim 1, wherein the halogen atom is bromine.

8. A compound as claimed in claim 1, wherein $R^3$ is hydrogen.

9. A compound as claimed in claim 1, wherein $R^3$ is 2-pyridyl.

10. A compound as claimed in claim 1, wherein $R^1$ and $R^2$ are each hydrogen or methyl.

11. A compound as claimed in claim 1, wherein $R^3$ is hydrogen.

12. A compound as claimed in claim 1, wherein the ring A is substituted in the 2-position by a halogen atom.

13. A compound as claimed in claim 1, wherein Py is a 2-pyridyl group.

14. A compound according to claim 1, namely 11,12-dihydro-13a-(2-pyridyl)-9H,13aH-oxazolo[3,2-d]-s-triazolo-[1,5-a][1,4]benzodiazepine-7-carboxamide.

15. A compound according to claim 1, namely 2-bromo-11,12-dihydro-12-methyl-13a-(2-pyridyl)-9H,13a H-oxazolo[3,2-d]-s-triazolo[1,5-a][1,4]benzodiazepine-7-carboxamide.

16. A compound according to claim 1, namely 11,12-dihydro-12-methyl-13a-(2-pyridyl)-9H,13aH-oxazolo[3,2-d]-s-triazolo-[1,5-a][1,4]benzodiazepine-7-carboxamide.

17. A compound according to claim 1, namely 2-bromo-11,12-dihydro-13a-(2-pyridyl)-9H,13aH-oxazolo[3,2-d]-s-triazolo[1,5-a][1,4]benzodiazepine-7-carboxamide.

18. A compound according to claim 1, namely 2-bromo-11,12-dihydro-13a-(2-pyridyl)-9H,13a*H*-oxazolo[3,2-d]-s-triazolo[1,5-d][1,4]benzodiazepine-7-(N-methyl)carboxamide.

19. A compound according to claim 1, namely 2-bromo-11,12-dihydro-13a-(2-pyridyl)-9H,13aH-oxazolo[3,2-d]-s-triazolo[1,5-a][1,4]benzodiazepine-7-N-(2-hydroxyethyl)carboxamide.

20. A heterocyclic compound of the formula:

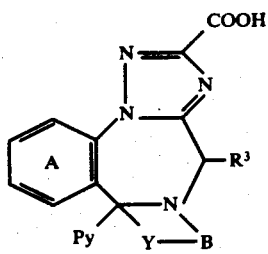

wherein R³ represents a hydrogen atom or a C₁–C₄ alkyl group; Py represents a pyridyl group; B represents an ethylene group or an ethylene group substituted by a C₁–C₄ alkyl group; Y represents oxygen; and ring A is either unsubstituted or substituted by a halogen atom, nitro, C₁–C₄ alkyl, C₁–C₄ alkoxy or trifluoromethyl or trichloro methyl group, or the corresponding C₁–C₄ alkyl ester thereof.

21. A pharmaceutical composition for use as a muscle relaxant, anticonvulsant, sedative and minor tranquilizer, which comprises a therapeutically effective amount of a compound as claimed in claim 1 together with a pharmaceutically acceptable carrier or diluent.

* * * * *

UNITED STATES PATENT OFFICE
CERTIFICATE OF CORRECTION

Patent No. 4,049,812     Dated September 20, 1977

Inventor(s) Yutaka Kuwada, et al

It is certified that error appears in the above-identified patent and that said Letters Patent are hereby corrected as shown below:

In the Abstract, third line from bottom: After "tranquilizers" insert --, etc.--.

Column 4, formula III: "CO" should be --C=O--.

line 19: Change "compriese" to --comprises--.

Column 7, lines 46,47: Change "ilolated" to --isolated--.

Column 11, line 55: Change "-s-tria" to -- -s-triazolo --.

line 66: Change "2bromo" to -- 2-Bromo --.

line 64: Change "[1,5- ]" to --[1,5-a]--.

UNITED STATES PATENT OFFICE
CERTIFICATE OF CORRECTION

Patent No. 4,049,812　　　　　　　　　Dated　September 20, 1977

Inventor(s)　Yutaka Kuwada, et al

It is certified that error appears in the above-identified patent and that said Letters Patent are hereby corrected as shown below:

Column 12, line 11:　"[1,5-A]" should be --[1,5-a]--.

line 30:　Insert --27.-- before "2-Bromo".

Column 16, line 36:　"anaylsis" should be --analysis--; "$C_{16}H_{14}ClN_5O_4$" should be --$C_{16}H_{14}ClN_5O_3$--.

Column 17, line 12:　"$C_{18}H_{16}BrBlN_4O_4$" should be --$C_{18}H_{16}BrClN_4O_4$--.

Column 19, line 17:　"oxazole" should be --oxazolo--.

Column 21, line 35:　Insert --(1)-- before "2-bromo".

Column 22, line 6:　"pyriduyl" should be --pyridyl--.

line 32:　"$R^3$" should be --Py--.

Column 24, line 1:　After "ethylene"(1st occurrence) delete "group".

Signed and Sealed this

Ninth Day of May 1978

[SEAL]

Attest:

RUTH C. MASON　　　　　　　LUTRELLE F. PARKER
Attesting Officer　　　Acting Commissioner of Patents and Trademarks